United States Patent
Jann et al.

(10) Patent No.: US 7,554,670 B2
(45) Date of Patent: Jun. 30, 2009

(54) SURFACE INSPECTION BY DOUBLE PASS LASER DOPPLER VIBROMETRY

(75) Inventors: Peter C. Jann, Santa Clara, CA (US); Wafaa Abdalla, San Jose, CA (US)

(73) Assignee: Seagate Technology LLC, Scotts Valley, CA (US)

( * ) Notice: Subject to any disclaimer, the term of this patent is extended or adjusted under 35 U.S.C. 154(b) by 130 days.

(21) Appl. No.: 11/654,929

(22) Filed: Jan. 17, 2007

(65) Prior Publication Data

US 2007/0165239 A1    Jul. 19, 2007

Related U.S. Application Data

(60) Provisional application No. 60/759,756, filed on Jan. 18, 2006.

(51) Int. Cl.
*G01B 9/02* (2006.01)

(52) U.S. Cl. ...................................... 356/487

(58) Field of Classification Search ................ 356/501, 356/485, 489, 486, 487, 511, 514
See application file for complete search history.

(56) References Cited

U.S. PATENT DOCUMENTS

| | | | | |
|---|---|---|---|---|
| 5,394,233 A | * | 2/1995 | Wang | 356/5.01 |
| 6,943,894 B2 | * | 9/2005 | Kitahara | 356/487 |

OTHER PUBLICATIONS

A. Vanderlugt & A.M. Bardos; *Design Relationships for Acousto-Optic Scanning Systems*; Applied Optics; vol. 31, No. 20, Jul. 10, 1992.

* cited by examiner

*Primary Examiner*—Hwa S Lee (Andrew)
(74) *Attorney, Agent, or Firm*—Dergosits & Noah LLP

(57) ABSTRACT

A double pass apparatus for detecting defects on a disk surface includes a light source that generates a light beam and a beamsplitter that splits the light beam into a first light beam portion and a second light beam portion. A modulator is provided that modulates the second light beam portion into a frequency shifted modulated light beam for illuminating the surface of the disk. The frequency shifted modulated light beam is twice reflected from the surface of the disk, thus doubling the frequency shift of the reflected light beam. A polarizing beamsplitter combines the first light beam portion with the reflected light beam portion providing an interference signal.

18 Claims, 4 Drawing Sheets

SURFACE INSPECTION BY DOUBLE PASS LASER DOPPLER VIBROMETRY

CROSS-REFERENCE TO RELATED PATENT APPLICATIONS

Embodiments of the present invention relate to U.S. Provisional Application Ser. No. 60/759,756, filed Jan. 18, 2006, entitled the same, the contents of which are incorporated by reference herein and which is a basis for a claim of priority.

BACKGROUND OF THE INVENTION

1. Field of the Invention

Embodiments of the present invention relate generally to the optical detection of defects in disk storage media. In particular, embodiments of the present invention relate to a method and apparatus for optically detecting defects on the surface disk storage media using a double pass configuration to significantly enhance disk surface event detection sensitivity.

2. Related Art

Disk drives typically employ one or more rotatable disks in combination with transducers supported for generally radial movement relative to the disks. Each transducer is maintained spaced apart from its associated disk, at a "flying height" governed by an air bearing caused by disk rotation. Present day transducer flying heights typically range from about 25 nm to about 50 nm, and experience velocities (relative to the disk, due to the disk rotation) in the range of 5-15 m/sec.

Effective recording and reading of data depend in part upon maintaining the desired transducer/disk spacing. Currently the amount of data that can be stored on the disk (i.e., the aerial density) is of great concern. As the aerial density increases and the flying height decreases, various surface defects in an otherwise planar disk surface of ever shrinking size become more and more significant. Thus, these defects or flaws can interfere with reading and recording, and present a risk of damage to the transducer, the disk recording surface, or both.

Therefore, the need arises for optically detecting, discriminating and measuring defects such as lumps, pits, scratches, micro-events, particles, etc. on the surface of disk storage media.

SUMMARY OF THE DISCLOSURE

Embodiments of the present invention address the problems described above and relate to a method and apparatus for optically detecting, discriminating and measuring defects on the surface of disk storage media.

According to one embodiment of the present invention, a double pass apparatus for detecting defects on a disk surface includes a light source that generates a light beam and a beamsplitter that splits the light beam into a first light beam portion and a second light beam portion. A modulator is provided that modulates the second light beam portion into a frequency shifted modulated light beam for illuminating the surface of the disk. The frequency shifted modulated light beam is twice reflected from the surface of the disk, thus doubling the frequency shift of the reflected light beam. A polarizing beamsplitter combines the first light beam portion with the reflected light beam portion providing an interference signal.

DETAILED DESCRIPTION OF THE PREFERRED EMBODIMENTS

A surface detection apparatus and method is described. In the following description, numerous details are set forth. It will be appreciated, however, to one skilled in the art, that embodiments of the present invention may be practiced without these specific details. In other instances, well-known structures and devices are shown in block diagram form, rather than in detail.

Generally speaking, laser Doppler vibrometry (LDV) is a non-contact technique to measure the defects on the surface of a moving object. LDV techniques are based on the use of an interferometer to measure the Doppler shift of light scattered by the moving object. The motion of the object relative to the light source causes a shift of the light's frequency as described by Doppler equations to be described in greater detail below. In other words, the basic LDV techniques compare a reflected beam of light to a reference beam of light to determine the Doppler frequency shift in the reflected beam of light. This Doppler shift is then used to measure the speed of the moving object.

Typically, the Doppler shift frequency is defined as: $Fd(t) = [2\cos(I)Vd(t)]/\lambda$ where $Fd(t)$ is the Doppler frequency shift; $I$ is the illumination angle of incidence; $V(t)$ is the axial velocity normal to the surface of a moving object; and $\lambda$ is the illumination wavelength.

The reference beam is a derivative or replica of an original transmitted beam. If the reference frequency is equal to the frequency of the transmitted beam, then a mixing process is referred to as homodyne detection and the resulting frequency is equal to the Doppler frequency. Alternatively, if the reference frequency is shifted by a known constant amount, then the mixing process is referred to as heterodyne detection and the resulting frequency has a frequency equal to the Doppler frequency plus a constant offset frequency.

One aspect of the present invention involves a heterodyne LDV defect inspection apparatus and method for collecting specular or non-scattered light that is reflected and Doppler shifted twice by the surface of the disk. This creates a double pass which doubles the induced Doppler frequency shift. The Doppler shift is proportion to the disk surface velocity. The disk surface velocity is the component normal to the disk surface.

Figure 1:
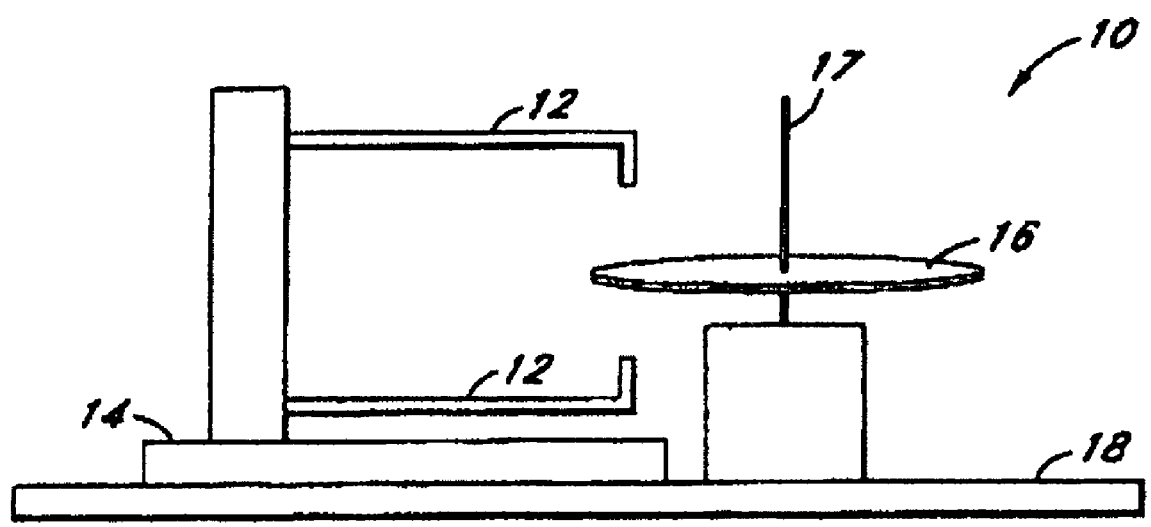
FIG. 1 illustrates generally a double pass advanced optical inspection system for inspecting disk surfaces according to one embodiment of the present invention.

An explanation will be given below regarding embodiments of the present invention while referring to the attached drawings. As shown in FIG. 1, an embodiment of a double pass advanced optical inspection system of the present invention, generally illustrated at 10, includes dual sensor heads 12 mounted on a carriage 14 and situated in relation to a magnetic disk substrate 16 such that one sensor head monitors a first surface of the disk 16 while the other sensor head monitors a second surface of the disk 16. The magnetic disk substrate 16 is rotated about an axis 17 during operation of the inspection apparatus.

The carriage 14 is preferably movable along a track 18 so that the optical inspection system of the present invention can be used to produce a scan of an entire disk as the carriage 14 is translated along the radius of the disk 16 as it is rotated. Each of the sensor heads 12 is capable of distinguishing bumps, pits, scratches and micro-events from surface contamination and quantitatively characterizing the geometry of the former while providing information regarding their location on the medium being examined.

Figure 2:
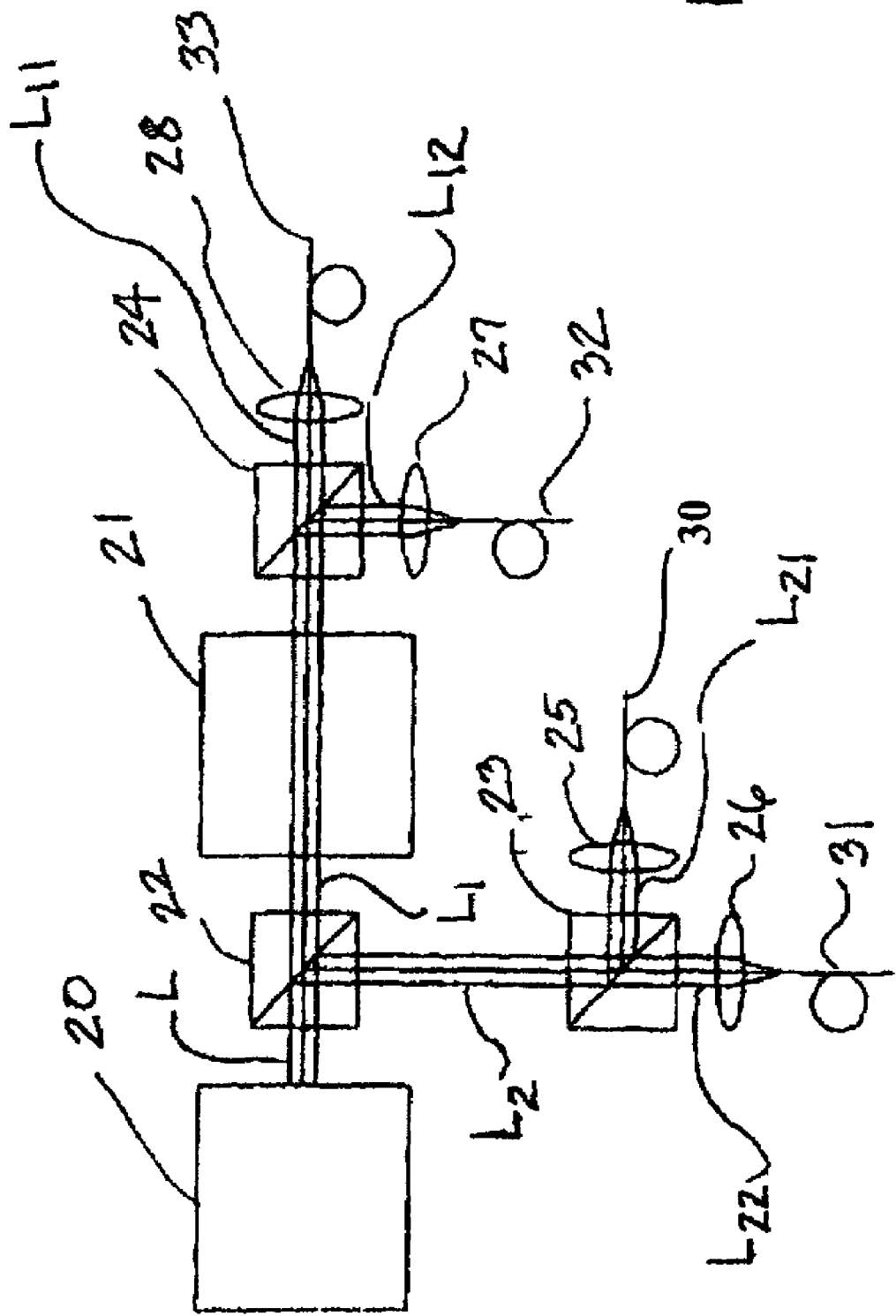
FIG. 2 illustrates a delivery module of a sensor optical illumination module for the double pass advanced optical inspection system according to one embodiment of the present invention.

FIG. 2 illustrates the delivery module of the sensor optical illumination module for the sensor heads 12 of the double pass advanced optical inspection system according to one embodiment of the present invention. The delivery module includes a laser diode collimator assembly (LDCA) 20, an acousto-optic modulator (AOM) 21, a first 50/50 beamsplitter 22, a second 50/50 beam splitter 23, a third 50/50 beamsplitter 24, a first lens 25, a second lens 26, and third lens 27 and a fourth lens 28. The delivery module also includes first, second, third and fourth polarization maintaining fibers, (PMF) 30-33, respectively. According to one embodiment of the present invention, the lenses may be aspheres and the LDCA 20 may be a semiconductor with a thermo-electric cooler and collimating optics as a radiation source. The laser diode of LDCA 20 is a single solid-state laser with a wavelength of 405 nm that is used to drive the top and bottom sensor heads 20 illustrated in FIG. 1.

The output beam L of the LDCA 20 is then split into two different beams, $L_1$ and $L_2$, at the first 50/50 beamsplitter 22. Regarding the path of the $L_1$ beam, in the embodiment shown in FIG. 2, the $L_1$ beam is initially frequency shifted by the AOM 21 positioned downstream of the first 50/50 beamsplitter 22. Upon being frequency shifted, the $L_1$ beam may be split into two different beams, $L_{11}$ and $L_{12}$, at the third 50/50 beamsplitter 24. Both the $L_{11}$ and $L_{12}$ beams are modulated by lenses 28 and 27, respectively, on to the fourth PMF 33 and third PMF 32, respectively. As an example, the AOM 21 imparts a 40 to 80 MHz sinusoidal carrier frequency on the field amplitude distribution of the $L_{11}$ and $L_{12}$ beams which are output to the fourth PMF 33 and third PMF 32. This carrier frequency or "offset frequency" imparted by the AOM 21 makes the interferometer an AC coupled heterodyne interferometer as opposed to a DC coupled homodyne interferometer, making the optical system impervious to stray light and permitting the use of frequency demodulation techniques.

Turning to the path of the $L_2$ beam, in the embodiment shown in FIG. 2, the $L_2$ beam is split into two different beams, $L_{21}$ and $L_{22}$, at the second 50/50 beamsplitter 23. Both the $L_{21}$ and $L_{22}$ beams are modulated by lenses 25 and 26, respectively, on to the first PMF 30 and second PMF 31, respectively. In an alternative embodiment of the present invention, free-space beamsplitting or fiber beamsplitting may be used depending on the type of laser used as the light source.

In a number of embodiments of the present invention, the first PMF 30 and the fourth PMF 33 are coupled to the upper sensor head and the second PMF 31 and the third PMF 32 are coupled to the lower sensor head. With this arrangement, approximately 15 mW of linearly polarized light will be delivered to each of the sensor heads 12. According to one embodiment of the present invention, high precision kinematics fiber couplers may be used to permit easy laser replacement.

Figure 3:
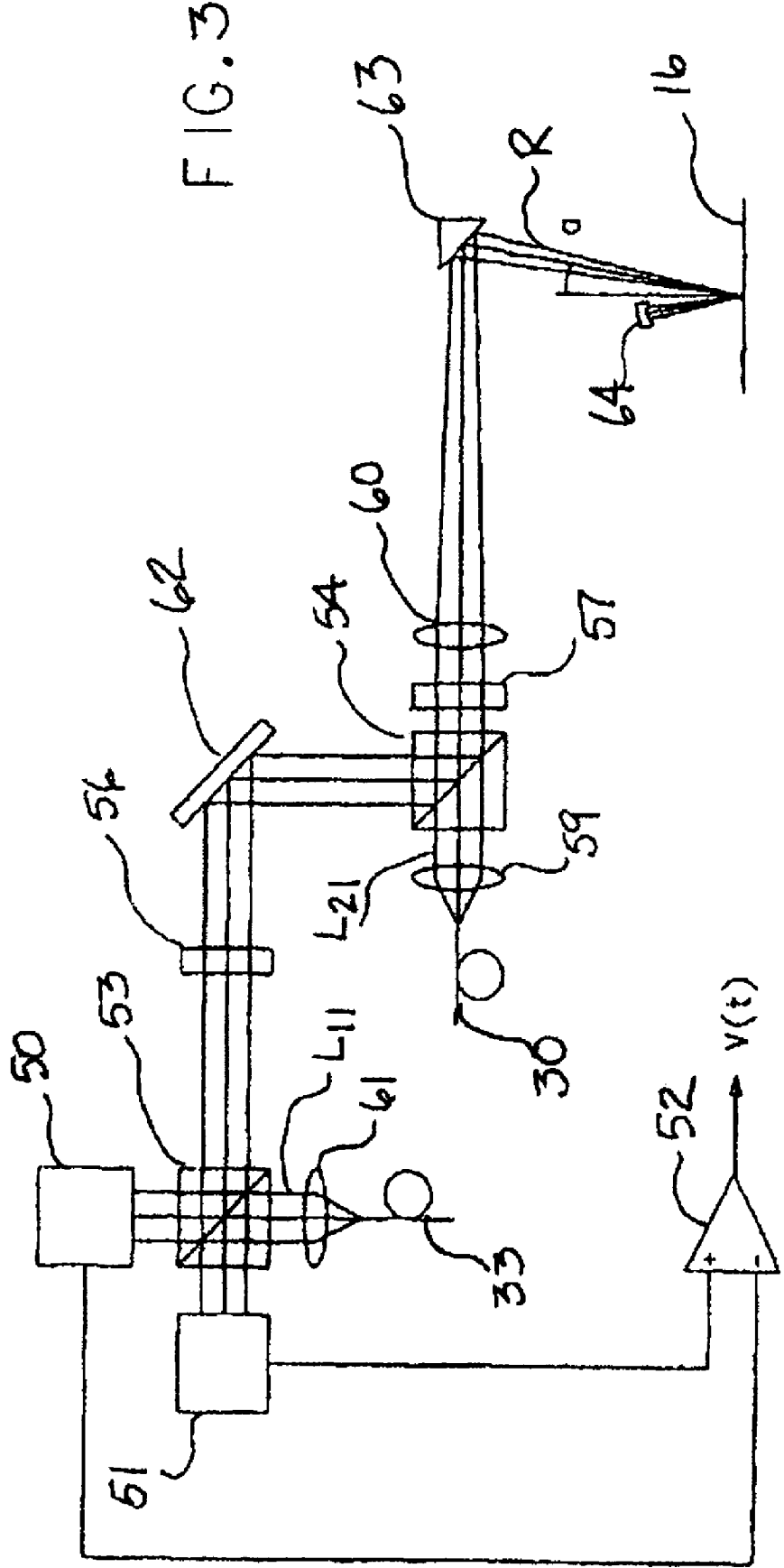
FIG. 3 illustrates the sensor optical illumination module and a sensor brightfield collection optical module for the double pass advanced optical inspection system according to one embodiment of the present invention.

Referring now to FIG. 3, which illustrates the sensor optical illumination module and a sensor brightfield collection optical module for the double pass advanced optical inspection system according to one embodiment of the present invention, only one sensor head 12 (the upper sensor head illustrated in FIG. 1) will be shown to avoid unnecessary duplication, since the two sensor heads are substantially the same. The sensor interferometer module for the double pass advance optical inspection system includes the first PMF 30 and the fourth PMF 33 from the sensor optical illumination module illustrated in FIG. 2, first and second photomultiplier tube (PMT)s 50 and 51, respectively, first and second polarized beamsplitter (PBS)s 53 and 54, respectively, and first, second and third lenses 59, 60 and 61, respectively.

The sensor optical illumination module and a sensor brightfield collection optical module for the double pass advance optical inspection system further includes a half-wave plate 56, a quarter-wave plate 57, flat mirror 62, prism mirror 63, spherical mirror 64 and the magnetic disk 16. Output beam $L_{11}$ from the fourth PMF 33 serves as the reference beam and the output beam $L_{21}$ from the first PMF 30 serves as the illumination beam for the system. Referring to the path of illumination beam $L_{21}$, the beam is first collimated by lens 59 and then split by the first PBS 59. Part of the beam is sent to the quarter-wave plate 57 and then to plano-convex lens 60. Afterwards, the beam is forwarded to the prism mirror 63 before being received by the magnetic disk 16.

According to one embodiment of the present invention, the magnetic disk 16 is illuminated from above by the illumination beam with a slightly elliptical diffraction limited spot of light that typically has a $1/e^2$ diameter of about 5 μm for example. This focused spot of light is produced by the plano-convex lens 60. As shown in FIG. 3, the plano-convex lens 60 has a small angle of incidence "a" large enough to permit a spherical mirror 64 to reflect the illumination beam back on to the magnetic disk 16. This creates the double pass which doubles the induced Doppler frequency shift.

The elliptical shape of the limited spot is typically made small so that the plane of incidence is parallel to either the circumferential or radial scan axes. This depends on the component arrangement required for the adjustable mount for the spherical mirror 64. The highest resolution is typically achieved when the plane of incidence is parallel to the radial scan axis. Circular polarization and near normal incidence typically insures that both circumferential and radial scratches will be equally illuminated.

The brightfield collection optical module (i.e., the prism mirror 63, the plano-convex lens 60, the quarter-wave plate 57, the first PBS 54, the flat mirror 62 and the half-wave plate 56) collects the specular or non-scattered light beam R that is reflected and Doppler shifted two times by the surface of the magnetic disk 16. This reflected specular collimated light beam R is then made to interfere with the reference beam $L_{11}$. Reference beam $L_{11}$ is first collimated by asphere lens. Afterwards, the collimated reference beam $L_{11}$ and the reflected specular collimated light beam R are fed to the second PBS 53 and an interference pattern is produced. The interference pattern is then square law detected by the first and second PMTs 50 and 51, respectively, arranged in a differential manner where the Doppler shifted 40 MHz carrier is observed in the interference pattern intensity distribution. The output signal from the first and the second PMTs are differential summed at differential amplifier 52 to produce a $2^{1/2}$ increase in the signal-to-noise ratio. This typically occurs when the system is detector shot noise limited.

With the double pass system discussed above, the Doppler frequency shift is now defined as: $Fd(t) = [4 \cos(a) Vd(t)]/\lambda$ where the illumination angle of incidence is the small angle of incidence "a" which is large enough to permit the spherical mirror 64 to reflect the illumination beam back onto the disk. The equation is doubled (i.e., (2)×2 cos(a)) because of the double pass system. The Doppler frequency shift for the double pass system is proportional to the disk surface velocity which is defined as: Vd(t)=A+Bsin[2π(Fd(t)+(carrier frequency))t].

Figure 4:
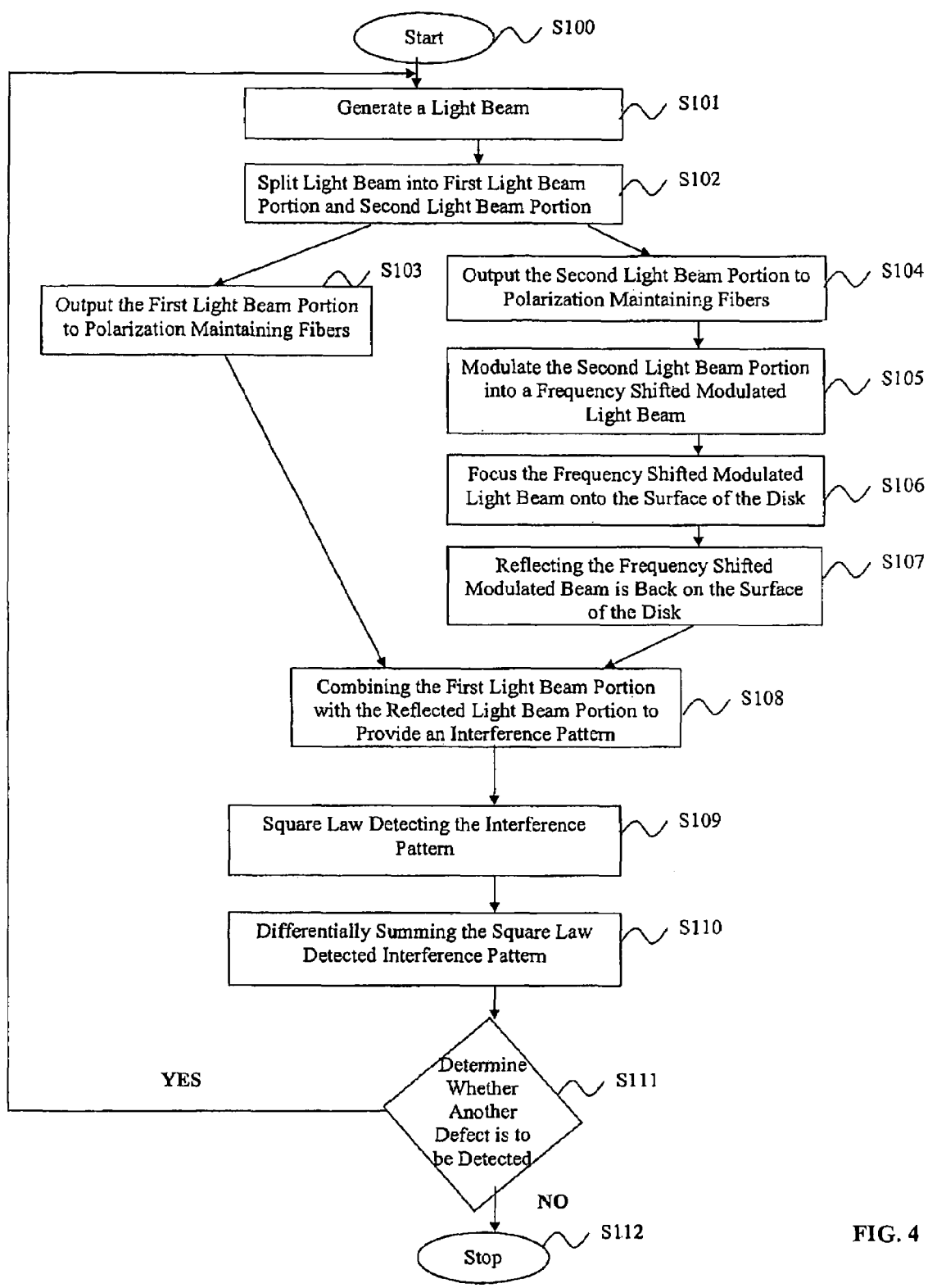
FIG. 4 is a flowchart depicting steps performed within a double pass apparatus for detecting defects on a disk surface in accordance with one embodiment of the present invention.

Referring now to FIG. 4, the operation of the double pass apparatus for detecting defects on a disk surface in accordance with the present invention as embodied in a method is depicted in a flowchart. The process begins from a start state S100 and proceeds to process step S101, where a light beam is generated. At process step S102, the light beam is split into a first light beam portion, which serves as a reference beam, and a second light beam portion, which serves as an illumination beam. According to one embodiment of the present invention, at process step S103, the first light beam portion is output to polarization maintaining fibers and at process step S104, the illumination beam is output to polarization maintaining fibers. The second light beam portion is later modulated into a frequency shifted modulated light beam for illuminating the surface of a disk at process step S105.

At process step S106, the frequency shifted modulated light beam is focused on the surface of the disk and provides an illumination spot on the surface of the disk. According to one embodiment of the present invention, the illumination spot has an elliptical shape. At process step S107, the frequency shifted modulated beam is reflected back on the surface of the disk. Thus, the frequency shifted modulated light beam is twice reflected from the surface of the disk, thereby doubling the frequency shift of the reflected light beam. At process step S108, the first beam portion is combined with the reflected light beam portion providing an interference pattern. At process step S109, the interference pattern is square law detected and at process step S110, the square law detected interference pattern is differentially summed. After a defect has been detected on the surface of the disk, the process proceeds to decision step S111 where it is determined whether another defect is to be detected. If another defect is to be detected, the process returns to process step S101, otherwise, the process terminates at state S112.

According to embodiments of the present invention, the double pass advanced optical inspection system effectively doubles the sensitivity or response of the laser Doppler vibrometer. The laser Doppler vibrometer in combination with the photomultiplier tubes increase the signal-to-noise ratio by a factor of two and thus increases detecting defects on the surface disk storage media.

What is claimed is:

1. A double pass apparatus for detecting defects on a disk surface, comprising:
   a light source that generates a light beam;
   a beamsplitter that splits the light beam into a first light beam portion and a second light beam portion;
   a modulator that modulates the second light beam portion into a frequency shifted modulated light beam for illuminating the surface of the disk,
   wherein the frequency shifted modulated light beam is twice reflected from the surface of the disk, doubling the frequency shift of a reflected light beam;
   a polarizing beamsplitter that combines the first light beam portion with the reflected light beam portion providing an interference pattern; and
   photomultiplier tubes that square law detect the interference pattern.

2. The double pass apparatus for detecting defects on a disk surface according to claim 1, wherein the photomultiplier tubes are arranged differentially.

3. The double pass apparatus for detecting defects on a disk surface according to claim 1, further comprising a lens to reflect the frequency shifted modulated light beam back onto the surface of the disk.

4. The double pass apparatus for detecting defects on a disk surface according to claim 1, further comprising a differential amplifier that differentially sums the square law detected interference pattern.

5. The double pass apparatus for detecting defects on a disk surface according to claim 1, wherein the light source is fiber optic coupled with polarization maintaining fibers.

6. The double pass apparatus for detecting defects on a disk surface according to claim 1, further comprising a plano-convex lens providing an illumination spot on the surface of the disk.

7. The double pass apparatus for detecting defects on a disk surface according to claim 6, wherein the plano-convex lens has an angle of incidence which allows a spherical mirror to reflect the frequency shifted modulated light beam back on to the surface of the disk.

8. The double pass apparatus for detecting defects on a disk surface according to claim 6, wherein the illumination spot has an elliptical shape.

9. A method for detecting defects on a disk surface, comprising:
   generating a light beam;
   splitting the light beam into a first light beam portion and a second light beam portion;
   modulating the second light beam portion into a frequency shifted modulated light beam for illuminating the surface of the disk,
   twice reflecting the frequency shifted modulated light beam from the surface of the disk,
   thereby doubling the frequency shift of a reflected light beam;
   combining the first light beam portion with the reflected light beam portion providing an interference pattern; and
   square law detecting the interference pattern.

10. The method for detecting defects on a disk surface according to claim 9, wherein twice reflecting the frequency shifted modulated light beam comprises reflecting the frequency shifted modulated light beam back onto the surface of the disk with a spherical mirror.

11. The method for detecting detects on a disk surface according to claim 9, further comprising differentially summing the square law detected interference pattern.

12. The method for detecting defects on a disk surface according to claim 9, further comprising coupling a fiber optic with polarization maintaining fibers.

13. The method for detecting defects on a disk surface according to claim 9, further comprising providing an illumination spot on the surface of the disk.

14. The method for detecting defects on a disk surface according to claim 13, wherein the illumination spot has an elliptical shape.

15. The method for detecting defects on a disk surface according to claim 9, further comprising providing a plano convex lens for creating an illumination spot on the surface of the disk.

16. The method for detecting defects on a disk surface according to claim 9, wherein the plano-convex lens has an angle of incidence which allows a spherical mirror to reflect the frequency shifted modulated light beam back on the surface of the disk.

17. The method for detecting defects on a disk surface according to claim 9, further comprising arranging photomultiplier tubes to increase optical inspection efficiency.

18. The method for detecting defects on a disk surface according to claim 9, wherein the photomultiplier tubes are arranged differentially.

* * * * *